United States Patent
Lee et al.

(10) Patent No.: US 7,502,274 B2
(45) Date of Patent: Mar. 10, 2009

(54) APPARATUS AND METHOD FOR SENSING TARGET TEMPERATURE

(75) Inventors: Hoon Lee, Seoul (KR); Hoe-Ju Chung, Yongin-si (KR)

(73) Assignee: Samsung Electroncis Co., Ltd., Suwon-si (KR)

( * ) Notice: Subject to any disclaimer, the term of this patent is extended or adjusted under 35 U.S.C. 154(b) by 248 days.

(21) Appl. No.: 11/481,739

(22) Filed: Jul. 6, 2006

(65) Prior Publication Data

US 2007/0133653 A1    Jun. 14, 2007

(30) Foreign Application Priority Data

Aug. 12, 2005    (KR) ...................... 10-2005-0074254

(51) Int. Cl.
*G11C 7/04*    (2006.01)

(52) U.S. Cl. .................. 365/211; 365/194; 365/222

(58) Field of Classification Search .................. 365/211, 365/194, 222, 233, 233.01; 327/158, 262, 327/378; 324/76.53, 76.54
See application file for complete search history.

(56) References Cited

U.S. PATENT DOCUMENTS

| | | | | |
|---|---|---|---|---|
| 4,710,648 | A * | 12/1987 | Hanamura et al. | 365/211 |
| 5,495,452 | A * | 2/1996 | Cha | 365/222 |
| 6,424,228 | B1 * | 7/2002 | Ahn et al. | 327/156 |
| 6,721,213 | B2 * | 4/2004 | Nakayama et al. | 365/194 |
| 6,735,137 | B2 * | 5/2004 | Jung et al. | 365/211 |
| 7,075,847 | B2 * | 7/2006 | Kim et al. | 365/222 |

* cited by examiner

*Primary Examiner*—David Lam
(74) *Attorney, Agent, or Firm*—Monica H. Choi (57) ABSTRACT

For sensing a target temperature, first and second temperature detectors generate first and second delay signals having negative and positive delay changes with temperature. A comparator senses the target temperature from the first and second delay signals such as by activating an output signal when the temperature is at least the target temperature.

20 Claims, 14 Drawing Sheets

APPARATUS AND METHOD FOR SENSING TARGET TEMPERATURE

BACKGROUND OF THE INVENTION

This application claims priority to Korean Patent Application No. 2005-74254, filed on Aug. 12, 2005 in the Korean Intellectual Property Office, the disclosure of which is incorporated herein in its entirety by reference.

1. Field of the Invention

The present invention relates generally to temperature sensing, and more particularly, to using multiple temperature detectors having positive and negative delay changes with respect to temperature for more accurately sensing a target temperature.

2. Description of the Related Art

In a dynamic random access memory (DRAM) device, data is stored by charge accumulation in a capacitor of a memory cell. However, leakage current through a PN junction of a MOS transistor reduces such charge accumulation potentially resulting in data loss. Accordingly, a refresh operation is performed for restoring the charge accumulation.

The leakage current in a DRAM memory cell generally increases with temperature. Accordingly, a refresh period is determined based on current leakage at high temperature, but such refresh period is also used at low temperatures resulting in unnecessary current consumption.

Alternatively, the refresh period is adjusted according to temperature for preventing unnecessary current consumption. To that end, a DRAM device includes a temperature sensing circuit for adjusting such a refresh period with temperature.

A temperature sensing circuit with a conventional band gap reference circuit has been widely used. However, this circuit is not used for low power applications due to the presence of a threshold voltage of a diode and a cascode type current mirror.

In particular, a diode is difficult to design for good characteristic in a CMOS process. If trimming points are used for a temperature sensing circuit sensing for a plurality of temperatures, i.e., multi-trimming points, a large resistor, a current mirror, a comparator, and the like are required resulting in difficult implementation.

Figure 1:
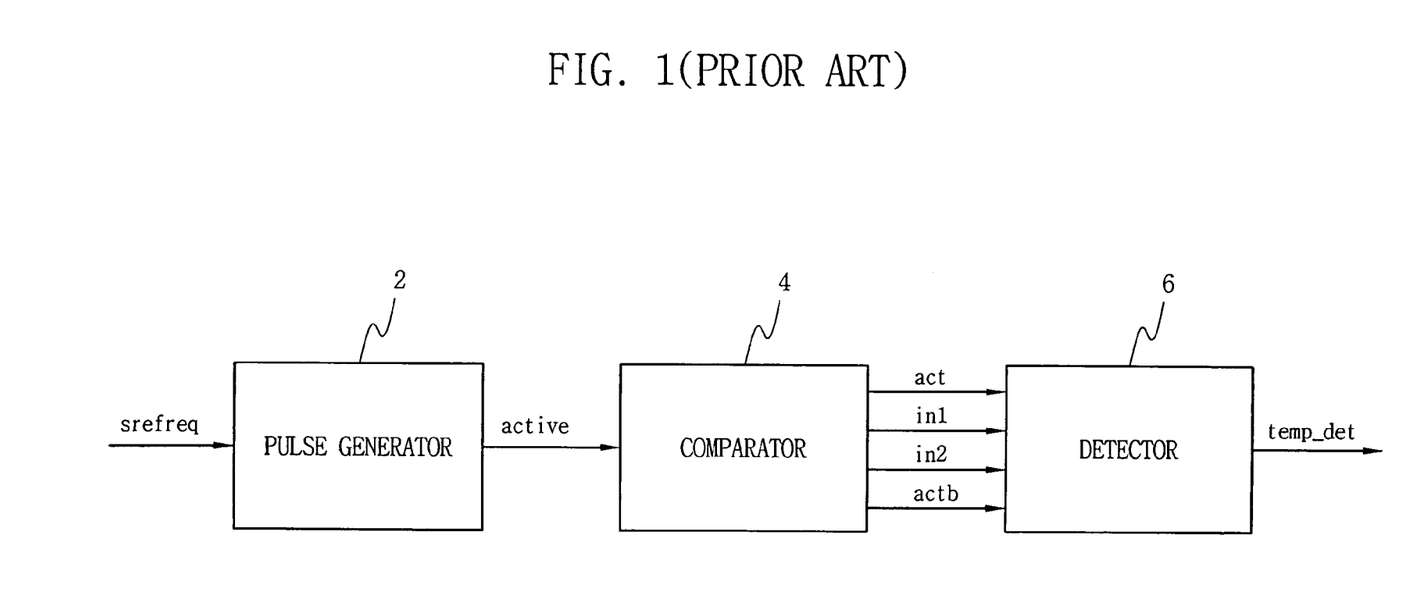
FIG. 1 shows a block diagram of a conventional temperature sensing circuit used in a semiconductor memory device.

To solve these problems, a conventional temperature sensing circuit has been implemented with inverter delay chains, as is now described in reference to the accompanying drawings. FIG. 1 shows a block diagram of such a conventional temperature sensing circuit used in a semiconductor memory device.

Referring to FIG. 1, the temperature sensing circuit includes a pulse generator 2, a comparator 4, and a detector 6. The pulse generator 2 receives a self refresh request signal srefreq to generate an active signal active. The comparator 4 receives the active signal active from the pulse generator 2 to generate control signals act and actb and delay signals in1 and in2. The detector 6 receives the control signals act and actb and the delay signals in1 and in2 to generate a temperature sensing signal temp_det.

Figure 2:
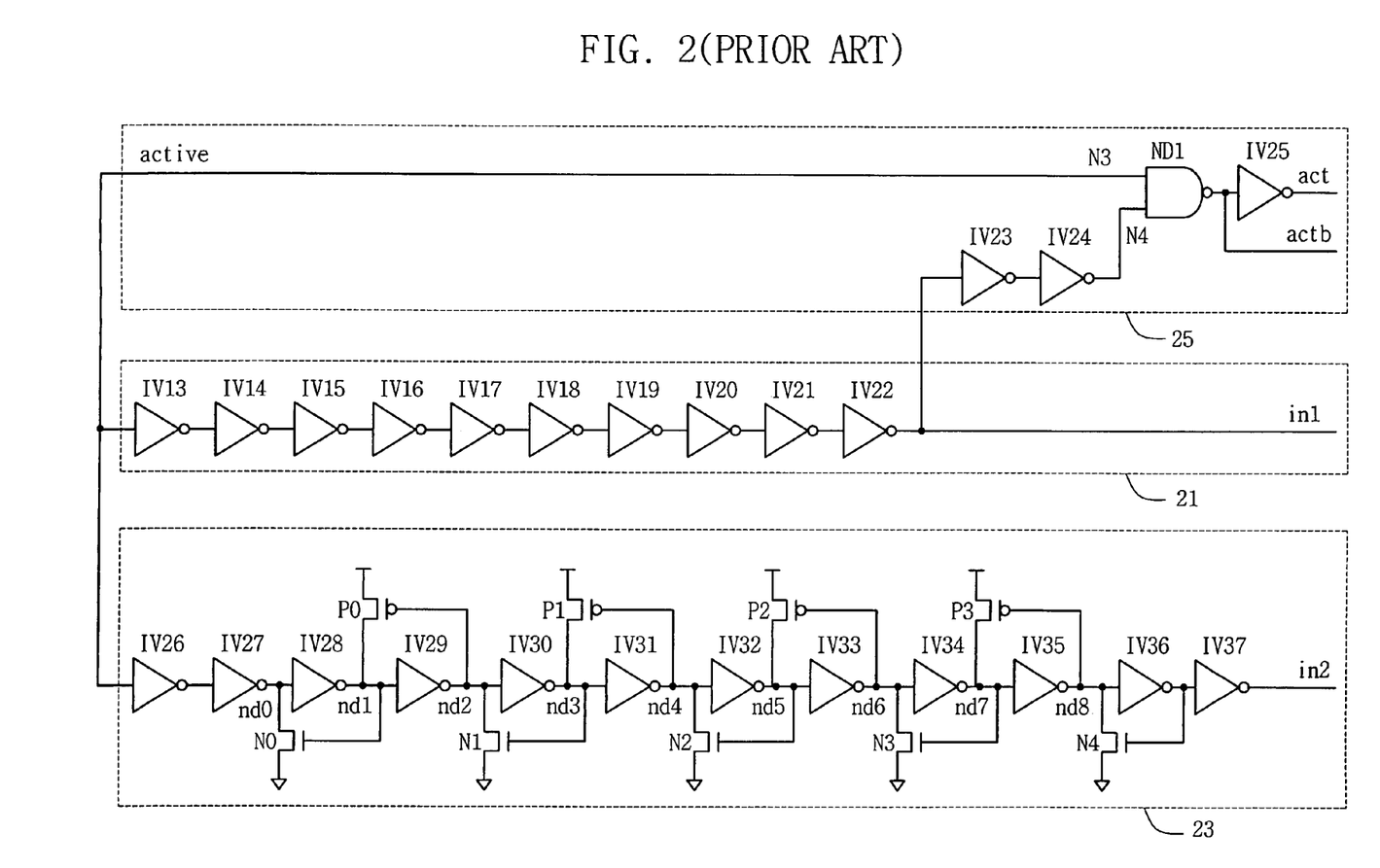
FIG. 2 shows a circuit diagram of the comparator of FIG. 1, according to the prior art.

FIG. 2 shows a circuit diagram of the comparator 4 of FIG. 1. Referring to FIG. 2, the comparator 4 receives the active signal active from the pulse generator 2. The active signal active is delayed through a first delay path 21 to generate delay signal in1 and through a second delay path 23 to generate delay signal in2. Each of the first delay path 21 and the second delay path 23 is implemented with a respective inverter delay chain, as illustrated in FIG. 2. The comparator 4 of FIG. 2 also includes a control circuit 25 that generates the control signals act and actb from the delay signal in1 and the active signal active.

The detector 6 activates the temperature sensing signal temp_det at a target temperature based on the delay signals in1 and in2. Such a temperature sensing signal temp_det is used for adjusting a self refresh period of a semiconductor memory device according to temperature.

Figure 3:
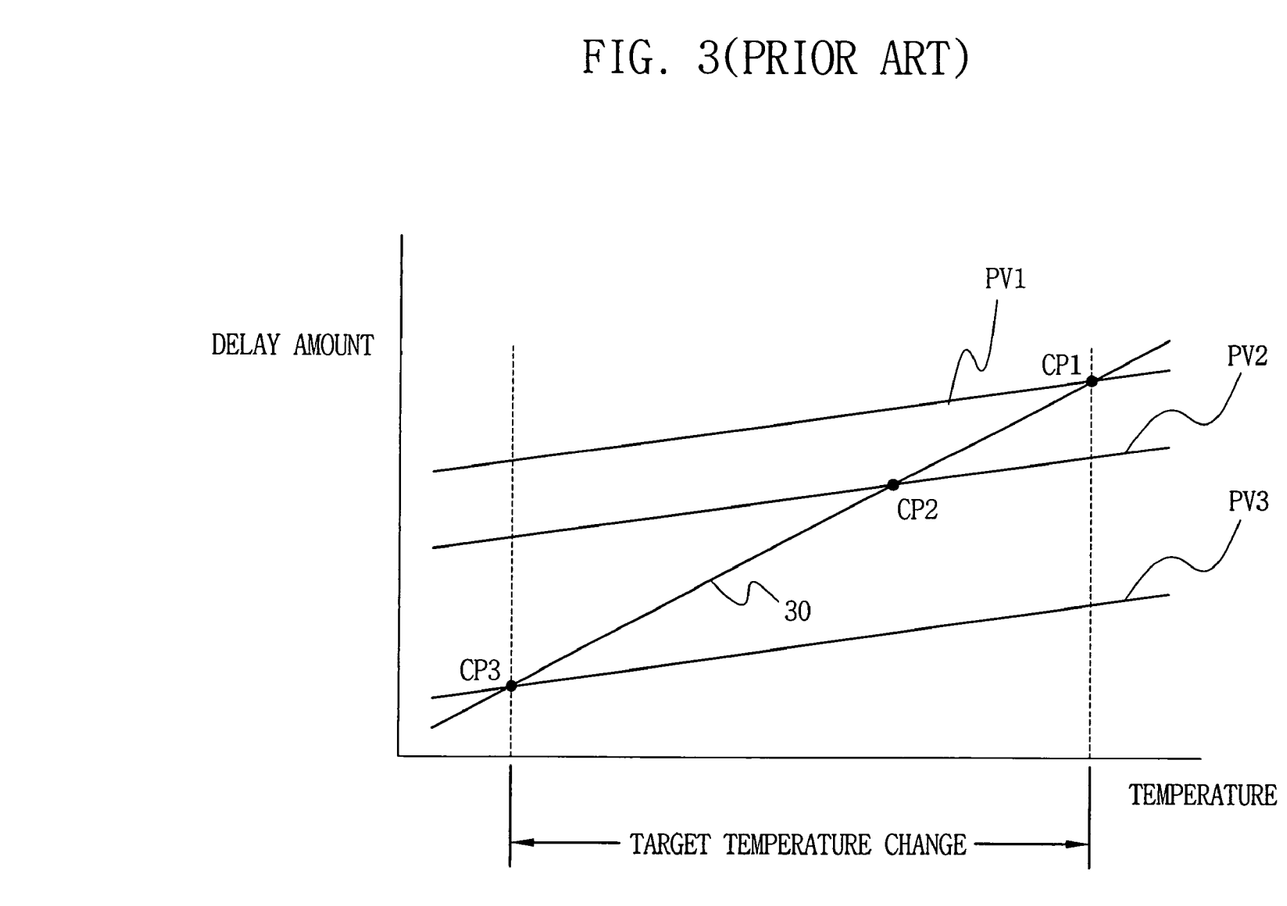
FIG. 3 shows delay characteristics with temperature for delay paths of FIG. 2 with fabrication process variation.

FIG. 3 shows graphs of delay amount versus temperature for the delay paths 21 and 23 of FIG. 2. Referring to FIG. 3, three graphs PV1, PV2 and PV3 are such delay characteristics with process variations in fabrication of one of the delay paths 21 or 23. The three graphs PV1, PV2 and PV3 have a substantially same slope but have different off-sets.

Further referring to FIG. 3, the other graph 30 is a delay characteristic for the other of the inverters 21 or 23. The three graphs PV1, PV2 and PV3 and the graph 30 intersect each other at points CP1, CP2 and CP3. Temperatures at such points CP1, CP2 and CP3 are the target temperatures sensed by the temperature sensing circuit with fabrication process variation.

FIG. 3 illustrates that such sensed target temperature varies widely with fabrication process variation such that a target temperature may not be sensed accurately in the prior art.

SUMMARY OF THE INVENTION

Accordingly, the present invention provides more accurate sensing of a target temperature by using multiple delay paths having both positive and negative delay characteristics with temperature.

For sensing a target temperature according to an aspect of the present invention, a first temperature detector generates a first delay signal having a negative delay change with temperature, and a second temperature detector generates a second delay signal having a positive delay change with the temperature. Additionally, a comparator senses the target temperature from the first and second delay signals.

In an example embodiment of the present invention, the first temperature detector includes a first inverter delay chain biased at a first voltage, and the second temperature detector includes a second inverter delay chain biased at a second voltage higher than the first voltage.

In another embodiment of the present invention, the first and second temperature detectors delay an input signal with respective delays to generate the first and second delay signals. In an example embodiment of the present invention, the input signal is generated from a memory controller that indicates a refresh operation to be performed within a memory device such as a DRAM (dynamic random access memory) device.

In a further embodiment of the present invention, the comparator generates an output signal that is activated when the temperature is at least the target temperature. In an example embodiment, such an output signal is coupled to a memory controller for determining a refresh time period within a memory device.

In another embodiment of the present invention, the comparator includes a D flip flop having a data terminal receiving the first delay signal and having a clock terminal receiving the second delay signal.

In a further embodiment of the present invention, the second temperature detector generates a third delay signal having a positive delay change with the temperature. In that case, another comparator senses another target temperature from the first and third delay signals.

In this manner, because the first and second temperature detectors provide multiple delay paths with both positive and negative delay changes with temperature, the target temperature that is sensed has smaller deviation with fabrication process variation. Thus, the target temperature may be sensed more accurately.

BRIEF DESCRIPTION OF THE DRAWINGS

The above and other features and advantages of the present invention will become more apparent when described in detailed exemplary embodiments thereof with reference to the attached drawings in which.

The figures referred to herein are drawn for clarity of illustration and are not necessarily drawn to scale. Elements having the same reference number in FIGS. 1, 2, 3, 4, 5, 6, 7, 8, 9, 10, 11, 12, 13, and 14 refer to elements having similar structure and/or function.

DETAILED DESCRIPTION OF THE INVENTION

Figure 4:
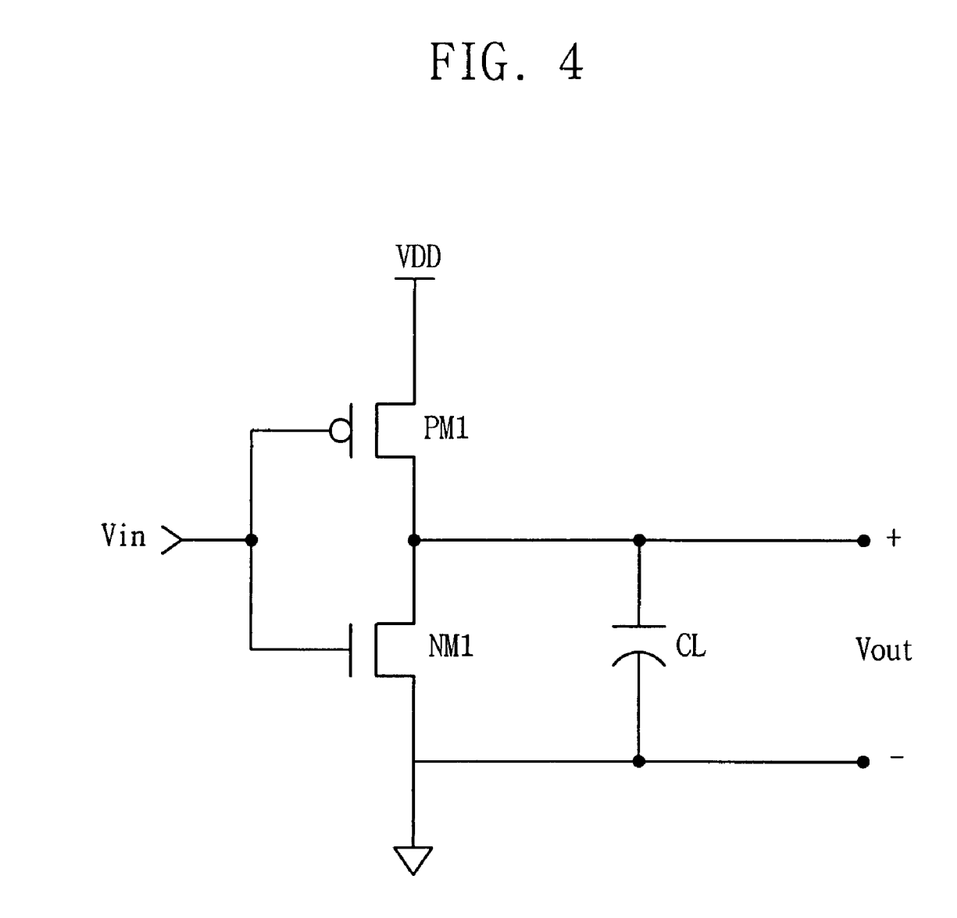
FIG. 4 shows a circuit diagram of an inverter for analyzing a delay characteristic with temperature for the inverter, according to an embodiment of the present invention.
Figure 5:
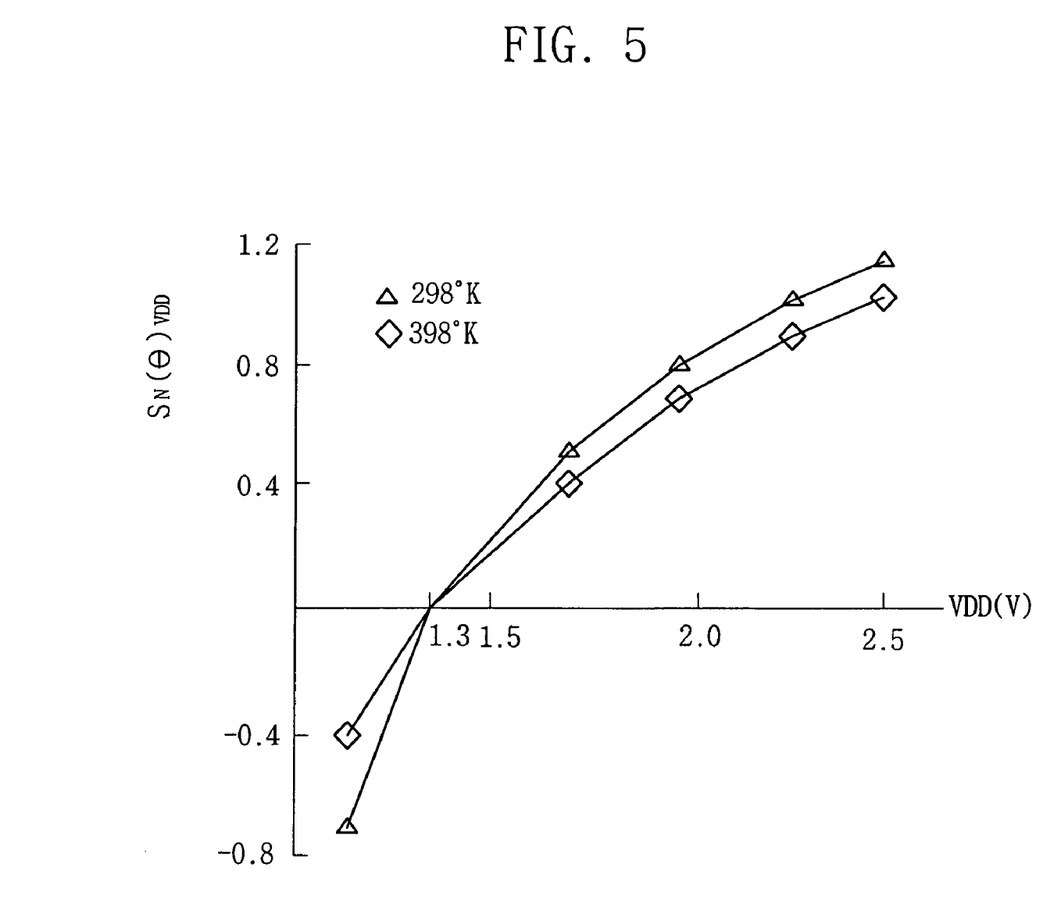
FIG. 5 shows a graph of delay coefficient with temperature for the inverter of FIG. 4, for embodiments of the present invention.

FIG. 4 shows a circuit diagram of an inverter for analyzing a delay characteristic with temperature for the inverter, according to an embodiment of the present invention. FIG. 5 shows graphs of delay coefficient for different temperatures of the inverter of FIG. 4, according to an embodiment of the present invention.

The inverter of FIG. 4 is formed with a PMOS transistor PM1 and an NMOS transistor NM1 configured as illustrated in FIG. 4. An inverted output Vout is generated across a load capicitor CL from an input signal Vin. Referring to FIGS. 4 and 5, a delay change with respect to an operating voltage VDD for the inverter increases with temperature below a critical VDD voltage of about 1.3 Volts and decreases with temperature above 1.3 Volts. In addition, the delay change with VDD is positive above 1.3 Volts, and negative below 1.3 Volts.

FIG. 5 illustrates a delay coefficient SN(G)VDD correlated with delay change that indicates a slope for a graph of delay versus temperature. A target temperature sensing apparatus of embodiments of the present invention uses such delay change characteristics for accurately sensing a target temperature.

Figure 6:
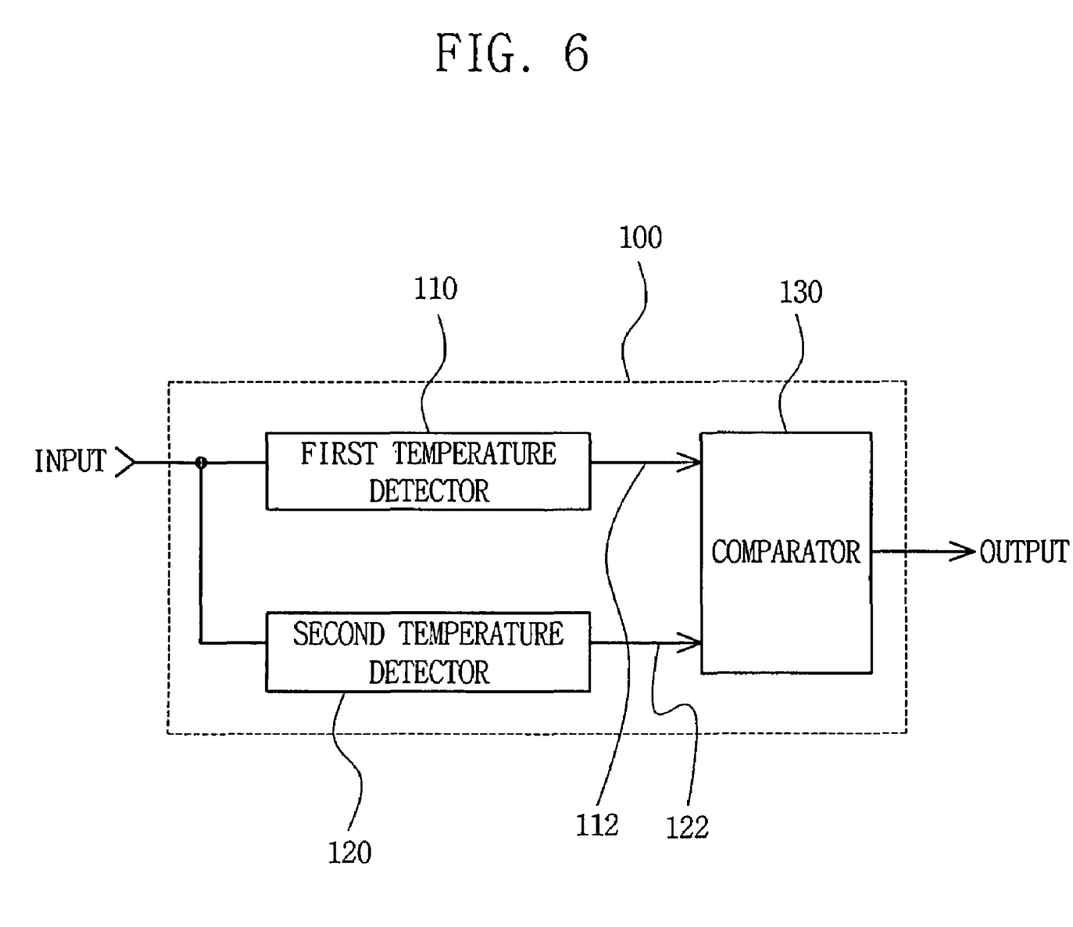
FIG. 6 shows a block diagram of a temperature sensing apparatus, according to an embodiment of the present invention.

FIG. 6 shows a block diagram of a target temperature sensing apparatus 100 according to an embodiment of the present invention. Referring to FIG. 6, the target temperature sensing apparatus 100 includes a first temperature detector 110, a second temperature detector 120, and a comparator 130.

The first temperature detector 110 receives an input signal INPUT to generate a first delay signal having a negative delay change with temperature. Referring to FIGS. 5 and 6, if the first temperature detector 110 were implemented with inverters, the first temperature detector 110 is biased at a first operating voltage VDD lower than 1.3V resulting in a negative slope of delay amount with temperature.

The second temperature detector 120 receives the input signal INPUT to generate a second delay signal having a positive delay change with temperature. Referring to FIGS. 5 and 6, if the second temperature detector 120 were implemented with inverters, the second temperature detector 120 is biased at a second operating voltage higher than 1.3V resulting in a positive slope of delay amount with temperature. The comparator 130 receives the first and second delay signals to generate a temperature sensing signal OUTPUT that is activated at a target temperature.

The input signal INPUT may be a self refresh request signal in a semiconductor memory device such as a DRAM (dynamic random access memory) device in particular. In that case, the temperature sensing signal OUTPUT is used to determine a refresh time period for a refresh operation in memory cells of the DRAM. Thus, the current consumption for such a refresh operation is determined by temperature to prevent unnecessary current consumption at lower temperatures.

Figure 7:
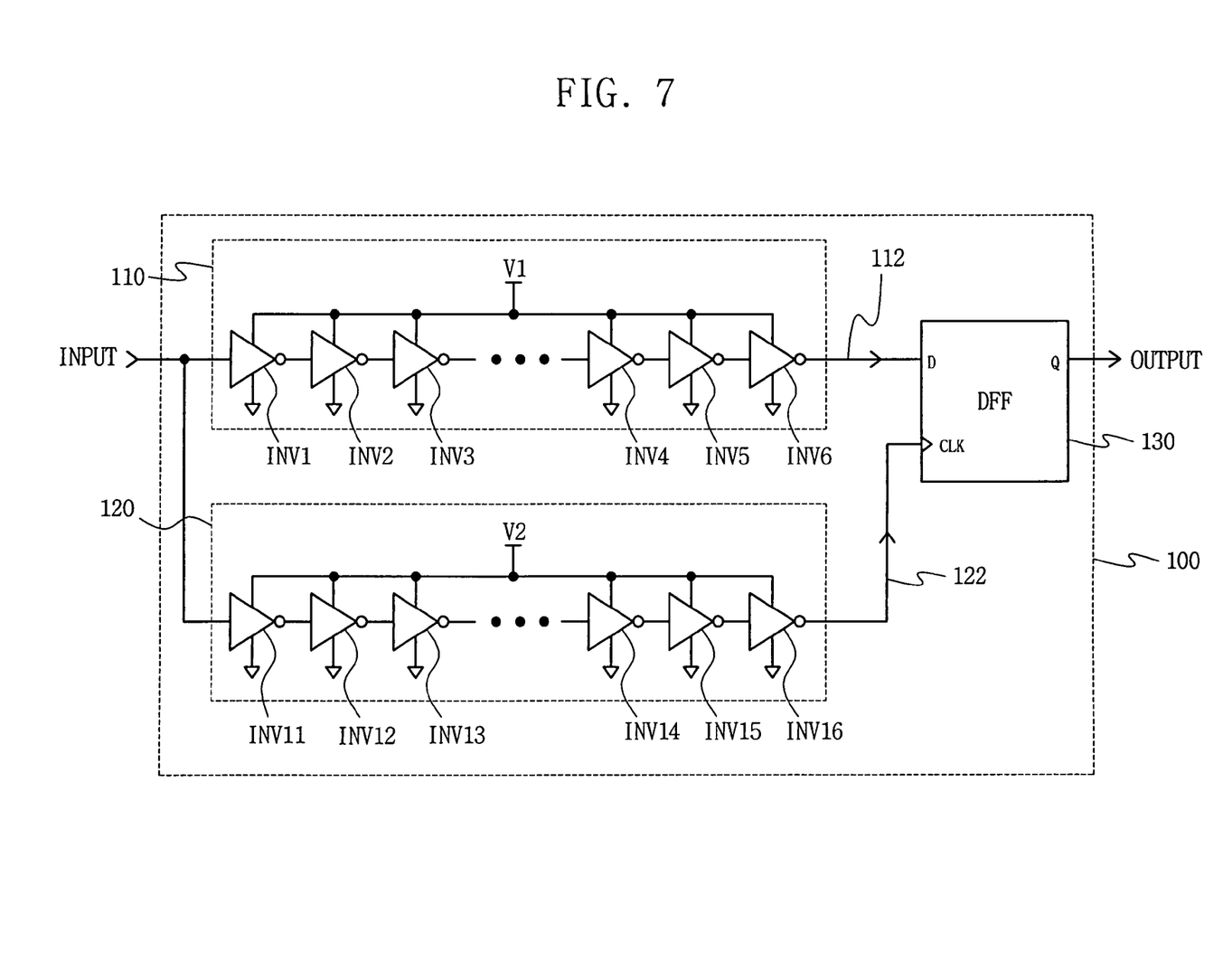
FIG. 7 shows a circuit diagram of the temperature sensing apparatus of FIG. 6, according to an embodiment of the present invention.
Figure 8:
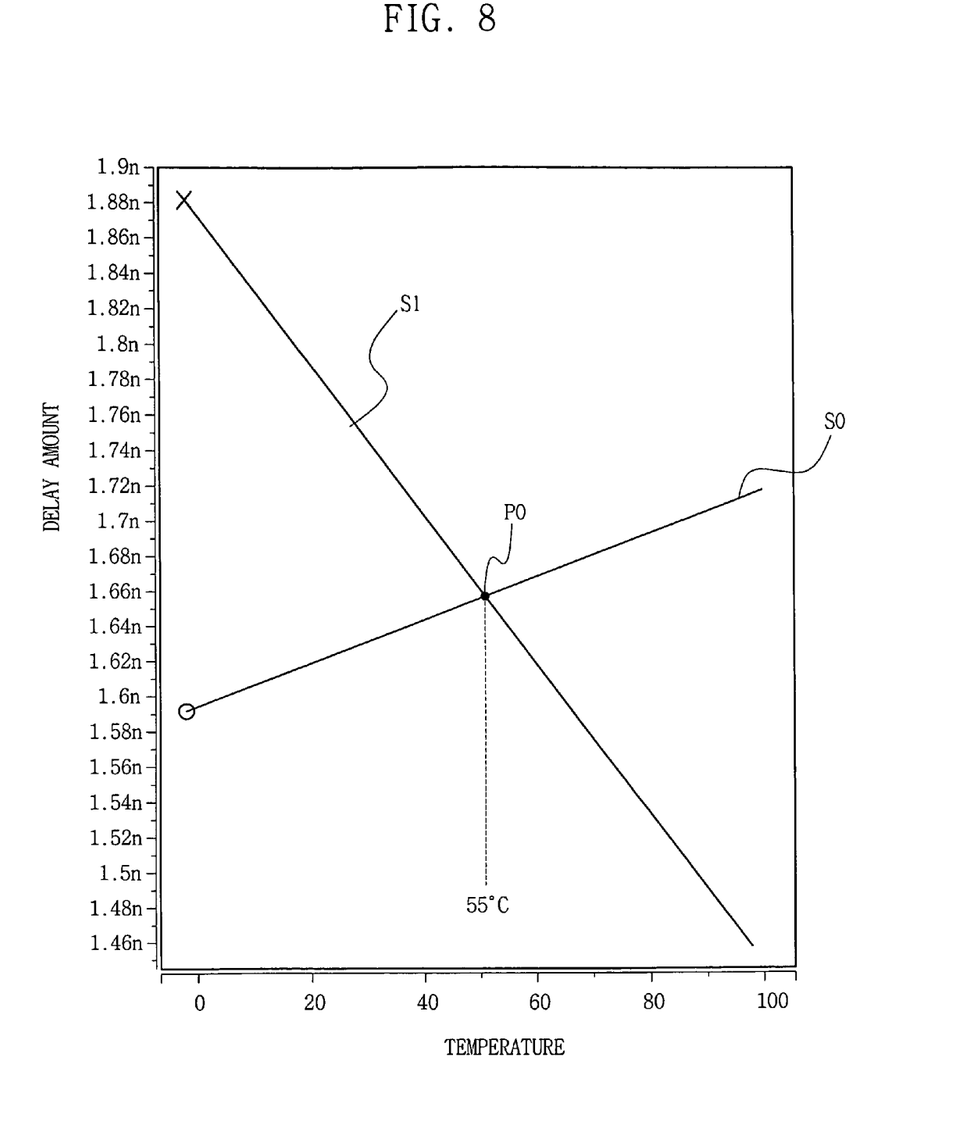
FIG. 8 shows graphs of delay characteristics for first and second inverter delay chains in FIG. 7, according to an embodiment of the present invention.
Figure 9:
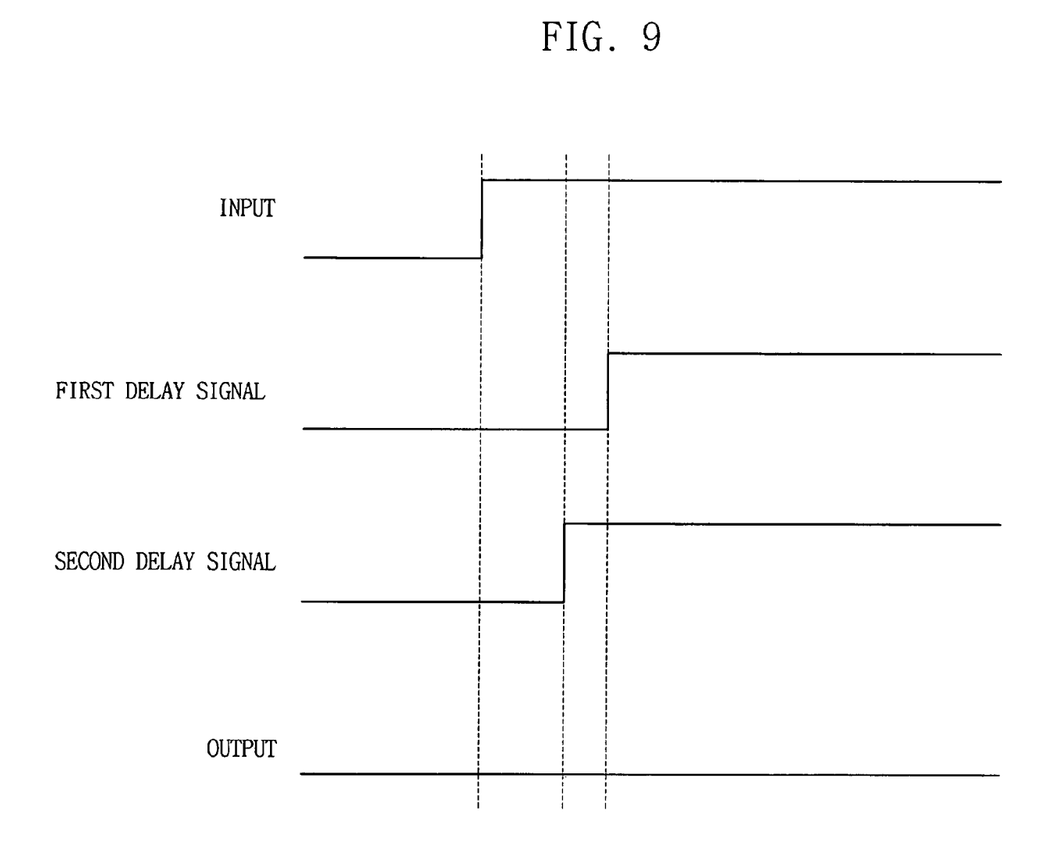
FIG. 9 shows timing diagrams of signals during operation of the temperature sensing apparatus of FIG. 7 at a temperature lower than a target temperature, according to an embodiment of the present invention.
Figure 10:
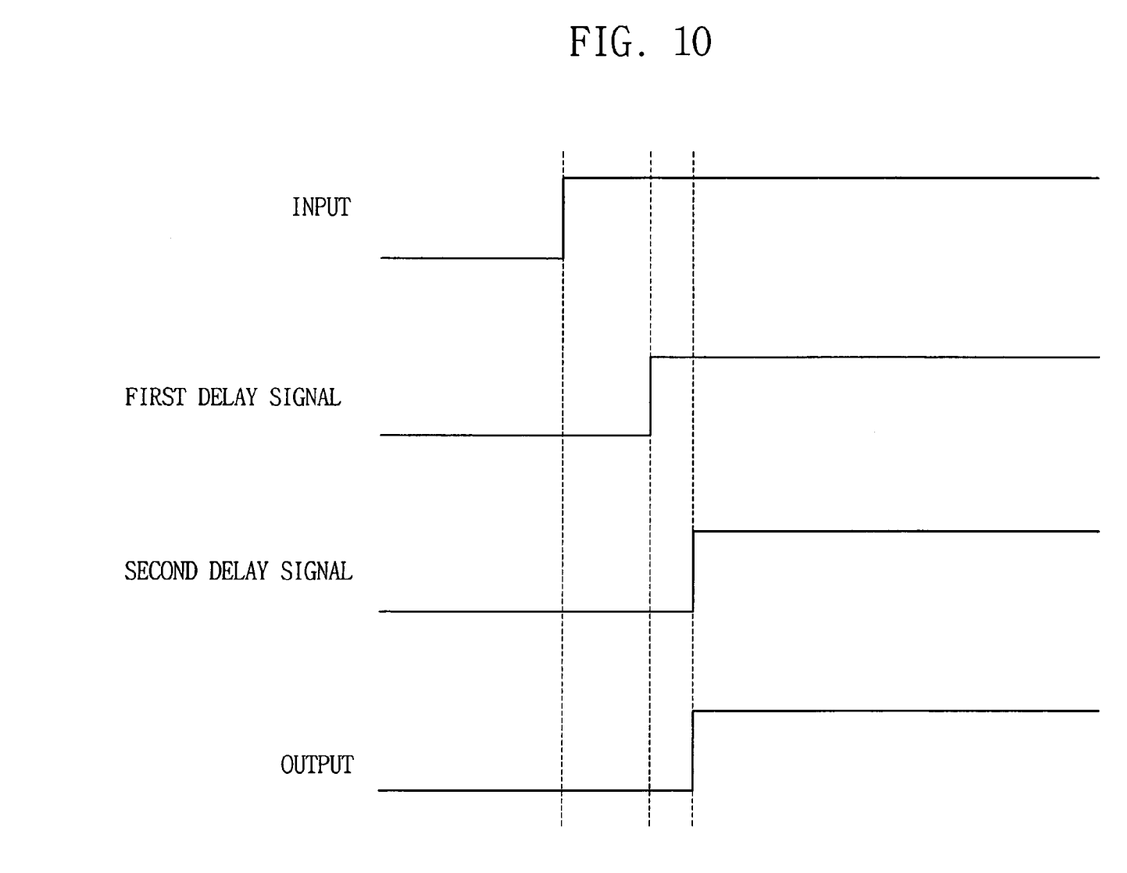
FIG. 10 shows timing diagrams of signals during operation of the temperature sensing apparatus of FIG. 7 at a temperature higher than the target temperature, according to an embodiment of the present invention.

FIG. 7 shows a circuit diagram for an example implementation of the temperature sensing apparatus 100 of FIG. 6. FIG. 8 shows graphs of delay amount with temperature for the first and second temperature detectors 110 and 120 of FIGS. 6 and 7. FIGS. 9 and 10 shows timing diagrams of signals during operation of the temperature sensing apparatus of FIGS. 6 and 7 at temperatures below and above, respectively, the target temperature according to an embodiment of the present invention.

Referring to FIG. 7, the first temperature detector 110 is implemented as a first inverter delay chain operating at a first operating voltage V1 lower than 1.3V resulting in a negative slope of delay amount with temperature. The second temperature detector 120 is implemented as a second inverter delay chain operating at a second operating voltage V2 higher than 1.3V resulting in a positive slope of delay amount with temperature.

The first inverter delay chain 110 includes a plurality of inverters INV1, INV2, ..., and INV6 coupled in series for delaying the input signal INPUT at a first inverter chain output node 112. The second inverter delay chain 120 includes a plurality of inverters INV11, INV12, ..., and INV16 coupled in series for delaying the input signal INPUT at a second inverter chain output node 122.

The comparator 130 is implemented as a D flip flop that receives the first and second delay signals from the first and second inverter delay chains 110 and 120 for generating the temperature sensing signal OUTPUT. The first delay signal from the first inverter delay chain 110 is coupled to a data terminal D of the D flip flop DFF, and the second delay signal from the second inverter delay chain 120 is coupled to a clock terminal CLK of the D flip flop DFF. D flip flops individually and in general are known to one of ordinary skill in the art.

Operation of the temperature sensing apparatus 100 is now described with reference to FIGS. 7, 8, 9, and 10. In FIGS. 9 and 10, the input signal INPUT is activated from logic low to logic high such as from a memory device for indicating a refresh operation to be performed. The first inverter delay chain 110 generates the first delay signal that is the input signal INPUT delayed by a first delay amount, and the second inverter delay chain 120 generates the second delay signal that is the input signal INPUT delayed by a second delay amount.

FIG. 8 illustrates a graph S1 of delay amount versus temperature for the first inverter delay chain 110, and the graph S1 has a negative slope. FIG. 8 also illustrates a graph S0 of delay amount versus temperature for the second inverter delay chain 120, and the graph S0 has a positive slope. The graphs S0 and S1 intersect at the target temperature (i.e. 55° C. in FIG. 8) to be sensed by the temperature sensing apparatus 100.

Referring to FIGS. 7, 8, and 9, when the temperature is below the target temperature, the first amount of delay of the first delay signal is greater than the second amount of delay of the second delay signal. Thus, the temperature sensing signal OUTPUT from the D flip flop DFF is not activated since the signal at the data terminal D is at logic low when the signal at the clock terminal CLK turns logic high.

Referring to FIGS. 7, 8, and 10, when the temperature reaches the target temperature (or is greater than the target temperature), the first amount of delay of the first delay signal is equal to or less than the second amount of delay of the second delay signal. Thus, the temperature sensing signal OUTPUT from the D flip flop DFF is activated since the signal at the data terminal D is at logic high when the signal at the clock terminal CLK turns logic high. The temperature sensing signal OUTPUT is activated to logic high as the second delay signal (i.e., the clock input CLK) turns logic high.

Thus, the temperature sensing signal OUTPUT being activated to logic high indicates that the temperature is at least at the target temperature. The memory device uses such information for determining an appropriate refresh time period for minimizing unnecessary current consumption during the refresh operation.

Figure 11:
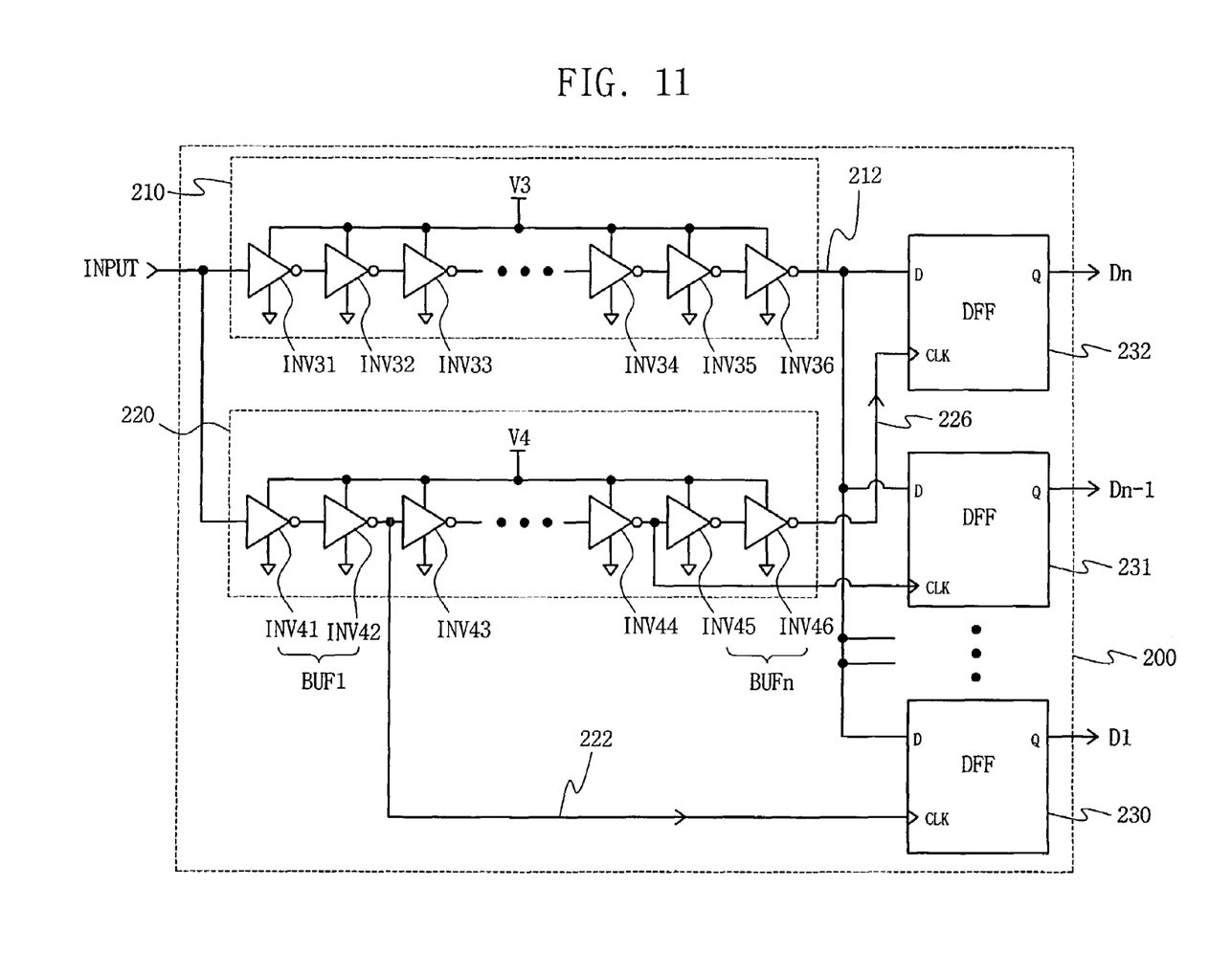
FIG. 11 shows a circuit diagram of a temperature sensing apparatus, according to another embodiment of the present invention.
Figure 12:
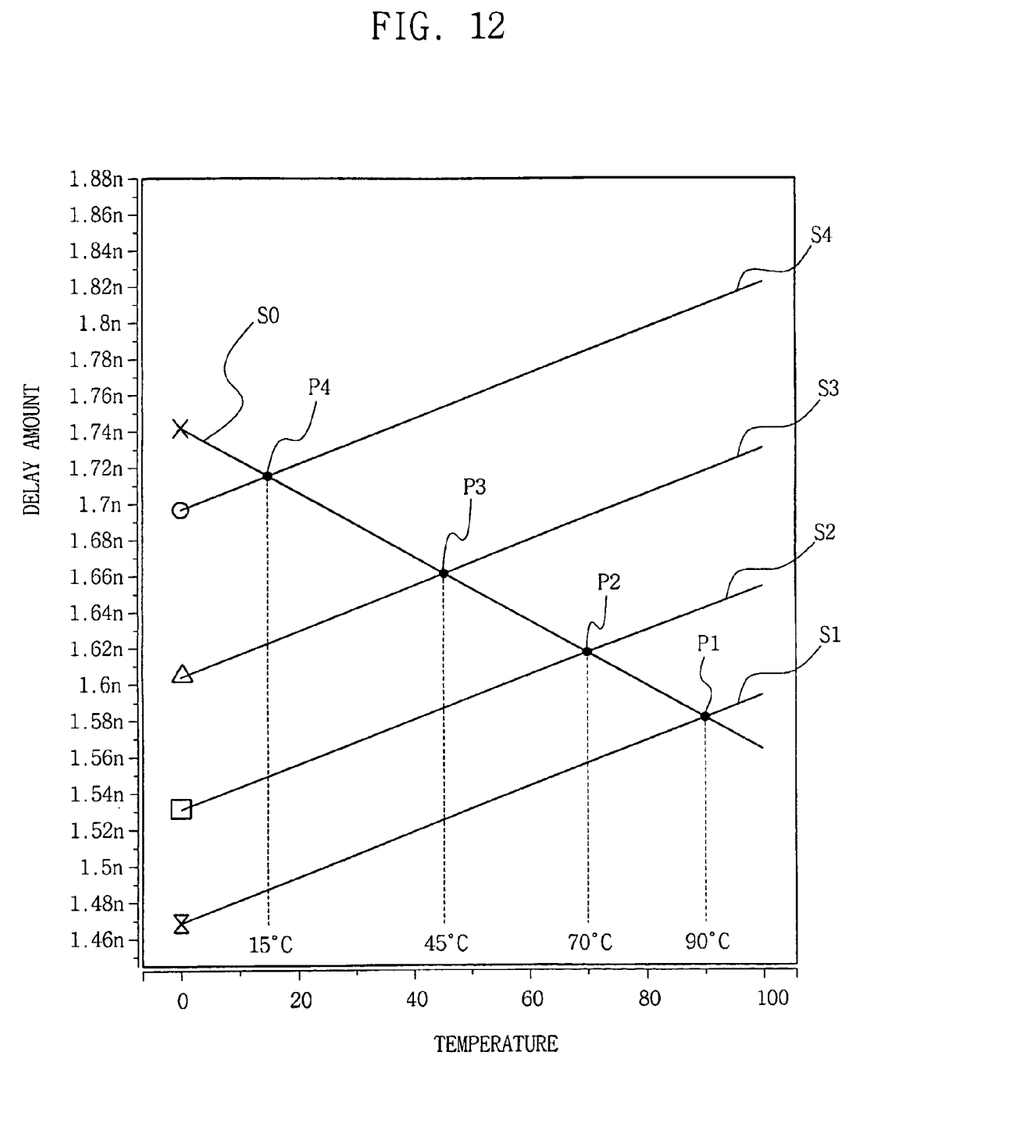
FIG. 12 shows graphs of delay characteristics of first and second inverter delay chains in FIG. 11, according to an embodiment of the present invention.

FIG. 11 shows a circuit diagram of a temperature sensing apparatus 200 according to another embodiment of the present invention. FIG. 12 shows graphs of delay amount versus temperature for the temperature sensing apparatus 200 of FIG. 11.

Referring to FIG. 11, the temperature sensing apparatus 200 includes a first inverter delay chain 210, a second inverter delay chain 220, and a plurality of comparing units 230, 231 and 232. Referring to FIGS. 11 and 12, the first inverter delay chain 210 is biased at a first operating voltage V3 resulting in a negative slope of delay amount with temperature as illustrated by a graph S0 in FIG. 12.

Further referring to FIGS. 11 and 12, the second inverter delay chain 220 is biased at a second operating voltage V4 resulting in a positive slope of delay amount with temperature as illustrated by graphs S1, S2, S3, and S4 in FIG. 12.

The second inverter delay chain 220 generates a plurality of delay signals having different delay amounts from the input signal INPUT as represented by the plurality of graphs S1, S2, S3, and S4 in FIG. 12. Each such delay signal is generated by a plurality of buffers BUF1 through BUFn, each formed by a respective set of even number of inverters coupled in series within the second inverter delay chain 220. Thus, the graphs S1, S2, S3, and S4 in FIG. 12 have a same slope but are offset from each-other.

Each of the comparing units 230, 231, and so on to 232 is a D flip flop that receives a delay signal generated by the first inverter delay chain 210 at the data terminal D (i. e., at node 212). Also, each of the comparing units 230, 231, and so on to 232 receives a respective one of the plurality of delay signals generated by the second inverter delay chain 220 at the clock terminal CLK (such as at nodes 222 and 226 for example). In this manner, each of the D flip flops DFF outputs a respective temperature sensing signal D1, ..., Dn-1, or Dn that is activated at a respective target temperature, as illustrated by the intersect points P1, P2, P3, and P4 in FIG. 12.

Figure 14:
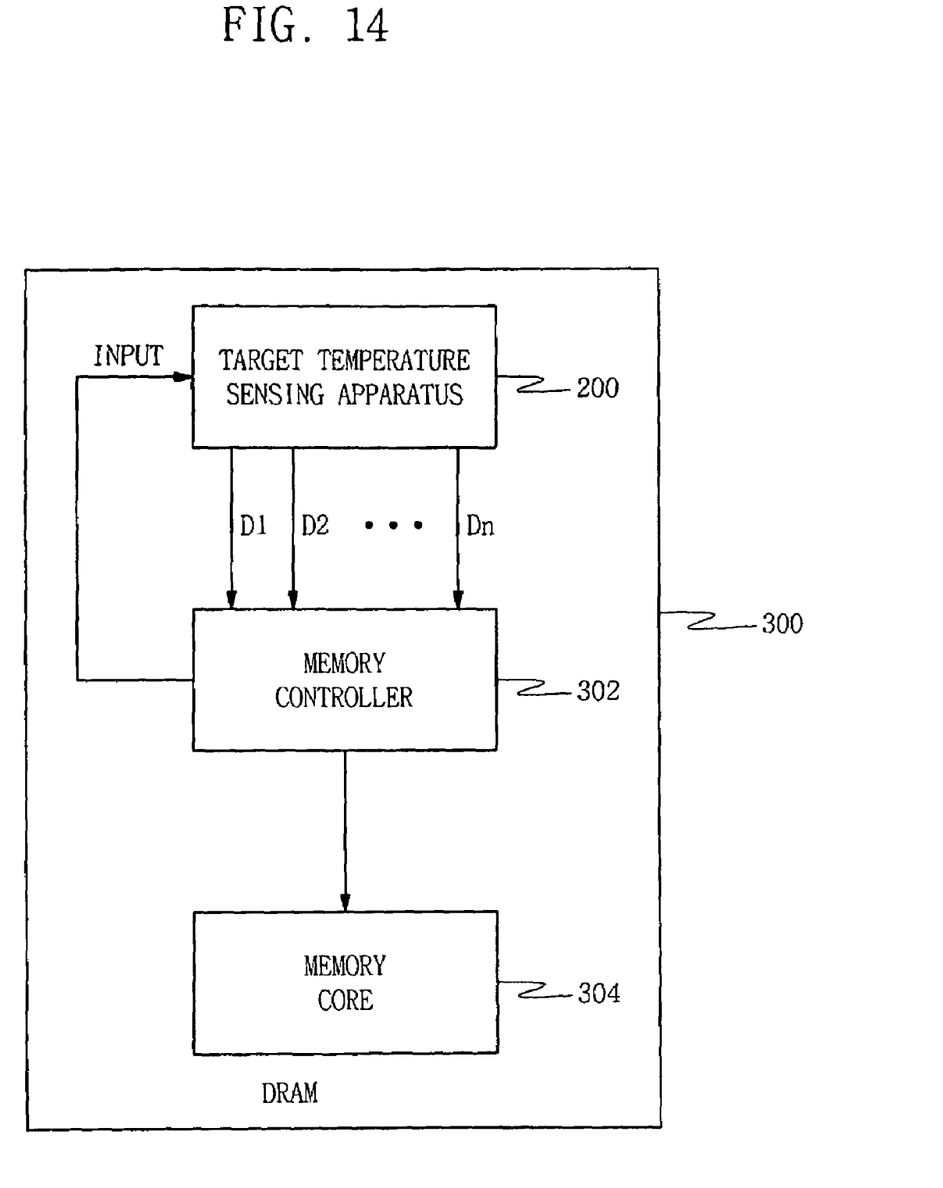
FIG. 14 shows a block diagram of a memory device having the temperature sensing apparatus of FIG. 11 formed therein, according to an embodiment of the present invention.

Accordingly, the temperature sensing apparatus 200 of FIG. 11 is capable of sensing for a plurality of target temperatures such as 15° C., 45° C., 70° C., and 90° C. as illustrated in FIG. 12. Such a temperature sensing apparatus 200 is advantageously applied in a semiconductor memory device that is a DRAM (dynamic random access memory) device 300 as illustrated in FIG. 14.

The DRAM device 300 has the temperature sensing apparatus 200 fabricated therein along with a memory controller 302 and a memory core 304. The memory controller 302 activates the input signal INPUT for indicating a refresh operation to be performed on the memory core 304. The temperature sensing apparatus 200 generates the temperature sensing signals D1, D2, ..., and Dn indicating whether the plurality of target temperatures has been reached. The memory controller uses such information for determining a refresh time period appropriate for the temperature of the memory device 300.

Figure 13:
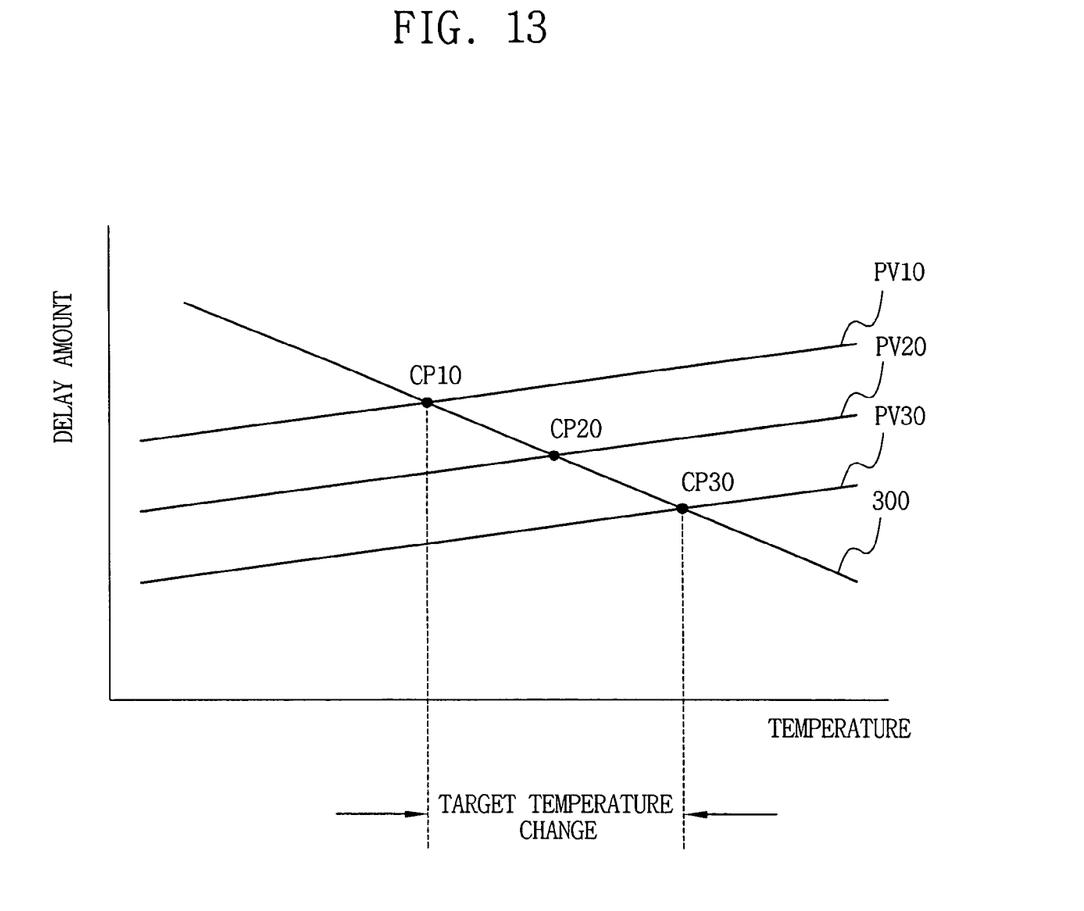
FIG. 13 shows graphs of delay characteristics with temperature for delay paths of FIG. 7 with fabrication process variation, according to an embodiment of the present invention.

In this manner, by using multiple inverter delay chains having positive and negative delay changes with temperature, the target temperature is sensed more accurately. For example, FIG. 13 shows graphs of delay amount versus temperature for such inverter delay chains with fabrication process variation. By using positive and negative delay changes with temperature, the range of the target temperature is less in FIG. 13 than that illustrated in FIG. 3 for inverter delay chains with only positive delay changes with temperature.

While the present invention has been particularly shown and described with reference to exemplary embodiments thereof, it will be understood by those of ordinary skill in the art that various changes in form and details may be made therein without departing from the spirit and scope of the present invention as defined by the following claims. For example, any numbers such as voltages or temperatures illustrated and specified herein are by way of example only, and the present invention may be practiced for other voltages and temperatures. In addition, any number of elements, or type of devices, or timing diagrams of signals illustrated and described herein are by way of example only. The present invention is limited only as defined in the following claims and equivalents thereof.

What is claimed is:

1. An apparatus for sensing a target temperature, comprising:
   a first temperature detector for generating a first delay signal having a negative delay change with temperature;
   a second temperature detector for generating a second delay signal having a positive delay change with the temperature; and
   a comparator for sensing the target temperature from the first and second delay signals,
   wherein the first delay signal is generated at a first output node, and wherein the second delay signal is generated at a second output node that is not connected to the first output node,
   and wherein the first temperature detector includes a first inverter delay chain biased at a first voltage for causing the first inverter delay chain to have the negative delay change with temperature, and wherein the second temperature detector includes a second inverter delay chain biased at a second voltage different from the first voltage with the second voltage being for causing the second inverter delay chain to have the positive delay change with temperature.

2. The apparatus of claim 1, wherein the second voltage is higher than the first voltage.

3. The apparatus of claim 1, wherein the first and second temperature detectors delay an input signal with respective delays to generate the first and second delay signals.

4. The apparatus of claim 3, wherein the input signal is generated from a memory controller that indicates a refresh operation to be performed within a memory device.

5. The apparatus of claim 1, wherein the comparator generates an output signal that is activated when the temperature is at least the target temperature.

6. The apparatus of claim 5, wherein the output signal is coupled to a memory controller for determining a refresh time period within a memory device.

7. The apparatus of claim 1, wherein the comparator comprises a D flip flop having a data terminal receiving the first delay signal and having a clock terminal receiving the second delay signal.

8. The apparatus of claim 1, wherein the second temperature detector generates a third delay signal having a positive delay change with the temperature, and wherein the apparatus further comprises:
   another comparator for sensing another target temperature from the first and third delay signals.

9. An apparatus for sensing a target temperature, comprising:
   means for generating first and second delay signals having negative and positive delay changes with temperature; and
   means for sensing the target temperature from the first and second delay signals,
   wherein the first delay signal is generated at a first output node, and wherein the second delay signal is generated at a second output node that is not connected to the first output node,
   and wherein a first inverter delay chain for generating the first delay signal is biased at a first voltage for causing the first inverter delay chain to have the negative delay change with temperature, and wherein a second inverter delay chain for generating the second delay signal is biased at a second voltage different from the first voltage with the second voltage being for causing the second inverter delay chain to have the positive delay change with temperature.

10. The apparatus of claim 9, wherein the first and second delay signals are generated by delaying an input signal with respective delays.

11. The apparatus of claim 10, wherein the input signal is generated from a memory controller that indicates a refresh operation to be performed within a memory device.

12. The apparatus of claim 9, wherein the means for sensing generates an output signal that is activated when the temperature is at least the target temperature.

13. The apparatus of claim 12, wherein the output signal is coupled to a memory controller for determining a refresh time period within a memory device.

14. The apparatus of claim 9, further comprising:
   means for generating a third delay signal having a positive delay change with the temperature; and
   means for sensing another target temperature from the first and third delay signals.

15. A method of sensing a target temperature, comprising:
   generating first and second delay signals having negative and positive delay changes with temperature;
   sensing the target temperature from the first and second delay signals;
   generating the first delay signal at a first output node:
   generating the second delay signal at a second output node that is not connected to the first output node:
   biasing a first inverter delay chain for generating the first delay signal at a first voltage that causes the first inverter delay chain to have the negative delay change with temperature: and
   biasing a second inverter delay chain for generating the second delay signal at a second voltage different from the first voltage with the second voltage being for causing the second inverter delay chain to have the positive delay change with temperature.

16. The method of claim 15, further comprising:
   delaying an input signal with respective delays to generate the first and second delay signals.

17. The method of claim 16, further comprising:
   receiving the input signal from a memory controller that indicates a refresh operation to be performed within a memory device.

18. The method of claim 15, further comprising:
   activating an output signal when the temperature is at least the target temperature.

19. The method of claim 18, further comprising:
   sending the output signal to a memory controller for determining a refresh time period within a memory device.

20. The method of claim 15, further comprising:
   generating a third delay signal having a positive delay change with the temperature; and sensing another target temperature from the first and third delay signals.

* * * * *